United States Patent
Green

(10) Patent No.: US 12,245,784 B2
(45) Date of Patent: *Mar. 11, 2025

(54) BASKET FOR A CATHETER DEVICE

(71) Applicant: Thrombolex, Inc., New Britain, PA (US)

(72) Inventor: Nicholas Green, Jupiter, FL (US)

(73) Assignee: THROMBOLEX, INC., New Britain, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/392,152

(22) Filed: Dec. 21, 2023

(65) Prior Publication Data

US 2024/0122614 A1    Apr. 18, 2024

Related U.S. Application Data

(63) Continuation of application No. 17/215,518, filed on Mar. 29, 2021, now Pat. No. 11,883,044, which is a
(Continued)

(51) Int. Cl.
*A61B 17/221* (2006.01)
*A61B 5/00* (2006.01)
(Continued)

(52) U.S. Cl.
CPC .............. *A61B 17/221* (2013.01); *A61B 5/00* (2013.01); *A61B 5/1076* (2013.01);
(Continued)

(58) Field of Classification Search
CPC ........ A61B 17/221; A61B 2017/22084; A61B 2017/22087; A61M 2025/0024; A61M 2025/0057; A61M 25/04

See application file for complete search history.

(56) References Cited

U.S. PATENT DOCUMENTS 5,059,178 A    10/1991 Ya
5,250,034 A    10/1993 Appling et al.
(Continued)

FOREIGN PATENT DOCUMENTS

WO    2017/181159 A1    10/2017
WO    2018033401 A1    2/2018

OTHER PUBLICATIONS

International Search Report and Written Opinion mailed Jan. 4, 2021, in Application No. PCT/US2020/052626.
(Continued)

*Primary Examiner* — Emily L Schmidt

(74) *Attorney, Agent, or Firm* — Fox Rothschild LLP

(57) ABSTRACT

The present disclosure relates to a basket for a catheter designed to be deployed in complex vasculature to optimally treat vascular and arterial disease conditions such as blood clots, blood emboli, and deep vein thrombosis. The basket may comprise a shaft with a plurality of cuts along a portion of its length to form a plurality of tines that provide support for a plurality of porous tubes to form the limbs of the basket. The limbs of the basket expand radially away from the longitudinal axis of the basket when the longitudinal length of the basket is reduced. The limbs may also be connected to a drug delivery system, and in this manner, baskets of the present disclosure allow for the use of both mechanical and pharmaceutical means of thrombolysis.

15 Claims, 9 Drawing Sheets

Related U.S. Application Data continuation of application No. 16/165,653, filed on Oct. 19, 2018, now Pat. No. 10,973,539, which is a continuation of application No. 15/808,649, filed on Nov. 9, 2017, now Pat. No. 10,105,154.

(51) Int. Cl.

| | | |
|---|---|---|
| *A61B 5/107* | (2006.01) | |
| *A61B 18/24* | (2006.01) | |
| *A61B 17/00* | (2006.01) | |
| *A61B 17/22* | (2006.01) | |
| *A61B 18/00* | (2006.01) | |
| *A61B 18/22* | (2006.01) | |
| *A61B 90/00* | (2016.01) | |
| *A61N 5/06* | (2006.01) | |

(52) U.S. Cl.
CPC .......... *A61B 5/6858* (2013.01); *A61B 18/245* (2013.01); *A61B 2017/00867* (2013.01); *A61B 2017/22084* (2013.01); *A61B 2017/22085* (2013.01); *A61B 2017/22087* (2013.01); *A61B 2017/2212* (2013.01); *A61B 2017/2215* (2013.01); *A61B 2018/00029* (2013.01); *A61B 2018/00267* (2013.01); *A61B 2018/0041* (2013.01); *A61B 2018/2211* (2013.01); *A61B 2090/064* (2016.02); *A61B 2217/007* (2013.01); *A61N 5/062* (2013.01); *A61N 2005/063* (2013.01)

(56) References Cited

U.S. PATENT DOCUMENTS

| | | | |
|---|---|---|---|
| 5,279,546 A | 1/1994 | Mische et al. | |
| 5,456,676 A | 10/1995 | Nelson et al. | |
| 5,591,137 A | 1/1997 | Stevens | |
| 5,599,328 A | 2/1997 | Stevens | |
| 5,616,203 A | 4/1997 | Stevens | |
| 5,651,170 A | 7/1997 | Stevens | |
| 5,843,022 A | 12/1998 | Willard et al. | |
| 5,957,865 A | 9/1999 | Backman et al. | |
| 5,957,901 A | 9/1999 | Mottola et al. | |
| 6,179,816 B1 | 1/2001 | Mottola et al. | |
| 6,206,868 B1 | 3/2001 | Parodi | |
| 6,263,236 B1 | 7/2001 | Kasinkas et al. | |
| 6,280,413 B1 | 8/2001 | Clark et al. | |
| 6,623,452 B2 | 9/2003 | Chien et al. | |
| 6,663,613 B1 | 12/2003 | Evans et al. | |
| 6,852,097 B1 | 2/2005 | Fulton, III | |
| 6,955,661 B1 | 10/2005 | Herweck et al. | |
| 8,187,222 B2 | 5/2012 | Weber et al. | |
| 8,556,880 B2 | 10/2013 | Freyman et al. | |
| 8,774,913 B2 | 7/2014 | Demarais et al. | |
| 8,945,143 B2 | 2/2015 | Ferrera et al. | |
| 9,427,300 B2 | 8/2016 | Angel et al. | |
| 10,105,154 B1 | 10/2018 | Green | |
| 10,123,814 B2 | 11/2018 | Bashir et al. | |
| 2001/0031981 A1 | 10/2001 | Evans et al. | |
| 2001/0044632 A1 | 11/2001 | Daniel et al. | |
| 2001/0049517 A1 | 12/2001 | Zadno-Azizi et al. | |
| 2002/0016564 A1 | 2/2002 | Courtney et al. | |
| 2003/0028210 A1 | 2/2003 | Boyle et al. | |
| 2003/0055401 A1 | 3/2003 | Larson et al. | |
| 2004/0133232 A1 | 7/2004 | Rosenbluth et al. | |
| 2005/0004594 A1 | 1/2005 | Nool et al. | |
| 2005/0228402 A1 | 10/2005 | Hofmann | |
| 2006/0259005 A1 | 11/2006 | Konstantino et al. | |
| 2007/0208367 A1 | 9/2007 | Fiorella et al. | |
| 2007/0249998 A1 | 10/2007 | Nair et al. | |
| 2009/0054918 A1 | 2/2009 | Henson | |
| 2009/0069789 A1 | 3/2009 | Freyman et al. | |
| 2010/0016832 A1 | 1/2010 | Thai et al. | |
| 2010/0036410 A1 | 2/2010 | Krolik et al. | |
| 2010/0069838 A1 | 3/2010 | Weber et al. | |
| 2010/0168647 A1 | 7/2010 | Tegg et al. | |
| 2010/0305678 A1 | 12/2010 | Alaswad | |
| 2010/0317921 A1 | 12/2010 | Marple et al. | |
| 2011/0077619 A1 | 3/2011 | Don Michael | |
| 2011/0264132 A1 | 10/2011 | Strauss et al. | |
| 2011/0276022 A1 | 11/2011 | O'Day | |
| 2012/0059309 A1 | 3/2012 | di Palma et al. | |
| 2012/0059356 A1 | 3/2012 | di Palma et al. | |
| 2013/0282084 A1 | 10/2013 | Mathur et al. | |
| 2014/0039484 A1 | 2/2014 | Leung | |
| 2014/0052103 A1 | 2/2014 | Cully et al. | |
| 2014/0074144 A1 | 3/2014 | Shrivastava et al. | |
| 2014/0155981 A1 | 6/2014 | Ferrera et al. | |
| 2015/0112376 A1 | 4/2015 | Molaei et al. | |
| 2016/0270813 A1 | 9/2016 | Chida | |
| 2016/0296245 A1 | 10/2016 | Yu | |
| 2018/0049761 A1 | 2/2018 | Bashir et al. | |
| 2019/0021751 A1 | 1/2019 | Bashir et al. | |
| 2019/0133618 A1 | 5/2019 | Green | |
| 2019/0167287 A1 | 6/2019 | Vale et al. | |

OTHER PUBLICATIONS

International Search Report and Written Opinion mailed Jan. 24, 2019, in Application No. PCT/US2018/060115.
International Search Report and Written Opinion mailed Jun. 27, 2017, in Application No. PCT/US2017/02828.

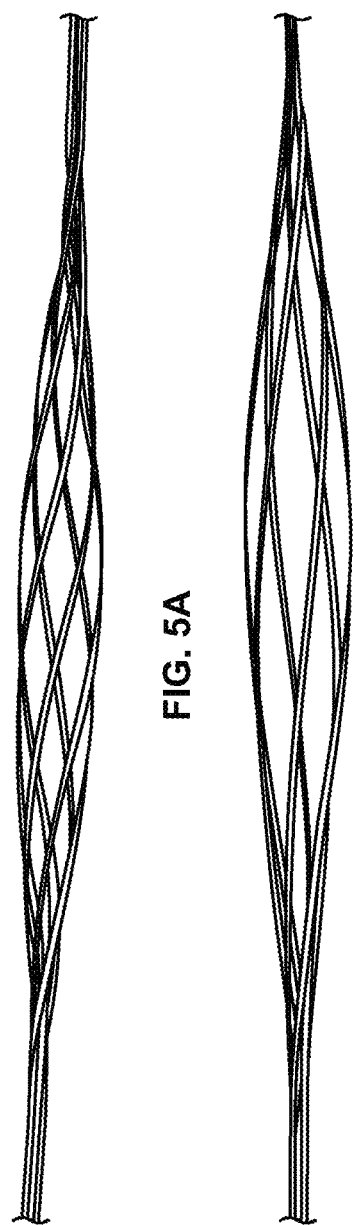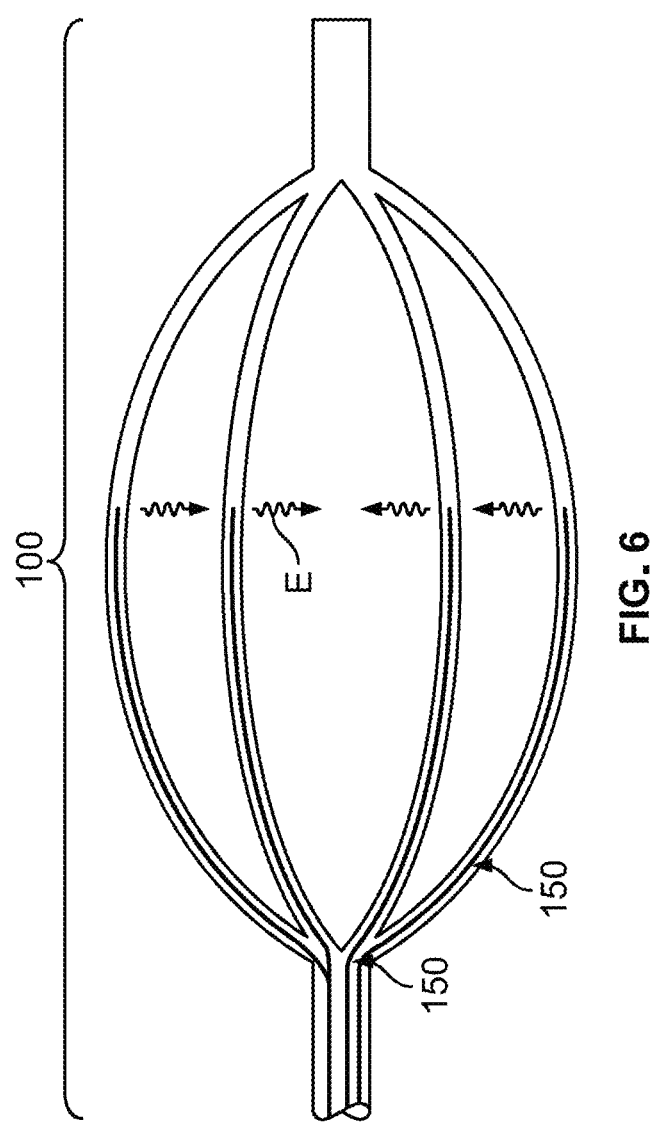

BASKET FOR A CATHETER DEVICE

CROSS-REFERENCE TO RELATED APPLICATIONS

This application is a continuation of U.S. patent application Ser. No. 17/215,518, filed Mar. 29, 2021, which is a continuation of U.S. patent application Ser. No. 16/165,653, filed Oct. 19, 2018, which is a continuation of U.S. patent application Ser. No. 15/808,649, filed Nov. 9, 2017, the disclosures of which are incorporated herein by reference in their entireties.

FIELD OF THE INVENTION

The present invention relates to mechanically deployable basket features for a catheter device, infusion catheters, and methods of treatment of pulmonary embolism and deep vein thrombosis.

BACKGROUND OF THE INVENTION

Conventional methods for catheter-directed thrombolysis involves infusing a clot dissolving medication via a single lumen infusion catheter, which is typically much smaller in diameter than the vessel in which it is placed. Additionally, because the clot has reduced or stopped the blood flow through the vessels, dispersion of the clot-dissolving medication is impaired. Catheter-directed thrombolysis devices may additionally employ expandable baskets to mechanically open a blood clot, but these expandable baskets typically function best in straight vessels and are not well adapted to the curved vascular. For example, in the case of a pulmonary embolism and the anatomy of the pulmonary artery, large blood clots are often lodged deep in the greater curvature of the artery and are difficult to treat. Concurrent monitoring of important vital signs within the occluded vessel, such as blood pressure, is also not possible during deployment of current catheter-directed thrombolysis devices.

What is needed in the art is an improved basket and infusion catheter that addresses the above limitations.

SUMMARY OF THE INVENTION

The present invention addresses the need mentioned above by providing deployable baskets, infusion catheters and methods for the treatment of thrombus in a blood vessel.

In one aspect, the present disclosure provides a basket for an infusion catheter comprising a shaft comprising a wall with an inner surface and an outer surface and a lumen extending between a distal end and a proximal end and defining a longitudinal axis, wherein a plurality of cuts along at least a portion of the shaft between the inner and outer surface of the wall form a plurality of tines, a plurality of tubes, each tube comprising a wall with an inner surface and an outer surface and a lumen extending between a distal end and a proximal end, wherein each of the plurality of tines of the shaft are disposed in the lumen of each of the plurality of tubes to form a plurality of limbs, and wherein the distal end of each of the plurality of limbs are attached and the proximal end of each of the plurality of limbs are attached.

In some embodiments, the limbs of the basket deploy from a first position to a second position when the longitudinal length of the basket is reduced. In some embodiments, the limbs of the basket are in a closed state in the first position. In some embodiments, the limbs of the basket expand radially away from the longitudinal axis when the longitudinal length of the basket is reduced.

In some embodiments, the shaft comprises a shape memory material. In some embodiments, the shape memory material is a nickel-titanium nitinol alloy.

In some embodiments, the plurality of cuts are formed by laser cutting. In some embodiments, the plurality of cuts are helical and have a rotation of at least 360 degrees over the length of the deployable infusion basket. In some embodiments, the plurality of helical cuts have a rotation of at least 450 degrees over the length of the deployable infusion basket. In some embodiments, the plurality of cuts do not extend to the proximal end of the shaft.

In some embodiments, each of the plurality of tubes is porous. In some embodiments, each of the plurality of tubes comprises a plurality of infusion ports extending between the inner surface and outer surface of the wall of the tube. In some embodiments, the infusion ports are holes having diameters between 0.001 and 0.006 inches.

In some embodiments, the basket is between three and eight inches in length. In some embodiments, the basket is about six inches in length.

In some embodiments, the basket further comprises a fiber optic material disposed within the lumen of at least one of the plurality of tubes.

In another aspect, the present disclosure provides a catheter comprising a basket comprising a shaft comprising a wall with an inner surface and an outer surface and a lumen extending between a distal end and a proximal end and defining a longitudinal axis, wherein a plurality of helical cuts along at least a portion of the shaft between the inner and outer surface of the wall form a plurality of tines, a plurality of tubes, each tube comprising a wall with an inner surface and an outer surface and a lumen extending between a distal end and a proximal end, wherein the each of the plurality of tines of the shaft are disposed in the lumen of each of the plurality of tubes to form a plurality of limbs, and wherein the distal end of each of the plurality of limbs are attached and the proximal end of each of the plurality of limbs are attached, an inner shaft comprising a wall with an inner surface and an outer surface and a lumen extending between a distal end and a proximal end, wherein the inner elongate shaft is disposed coaxially within the lumen of the shaft and is attached to the distal end of the basket, an outer shaft comprising a wall with an inner surface and an outer surface and a lumen extending between a distal end and a proximal end, wherein the outer shaft is disposed coaxially around the inner shaft to form a fluid compartment between the inner surface of the outer shaft and the outer surface of the inner shaft, and wherein the proximal end of the limbs of the basket are connected to the fluid compartment.

In some embodiments, the connection between the proximal end of the limbs of the basket and the fluid compartment comprises a seal disposed between the inner shaft and the proximal end of the plurality of limbs.

In some embodiments, the limbs of the basket deploy from a first position to a second position when the inner shaft is moved in a proximal direction. In some embodiments, the limbs of the basket expand radially away from the longitudinal axis when the inner shaft is moved in a proximal direction. In some embodiments, each of the plurality of tubes comprises a plurality of infusion ports extending between the inner surface and outer surface of the wall of the eluting arm. In some embodiments, the catheter further comprises a fiber optic material disposed within the lumen of the inner shaft or at least one of the plurality of tubes. In some embodiments, the basket further comprises an irradiation source.

Also provided herein is a method of catheter-directed thrombolysis, the method comprising providing a catheter comprising a basket comprising a shaft comprising a wall with an inner surface and an outer surface and a lumen extending between a distal end and a proximal end and defining a longitudinal axis, wherein a plurality of helical cuts along at least a portion of the shaft between the inner and outer surface of the wall form a plurality of tines, a plurality of tubes, each tube comprising a wall with an inner surface and an outer surface and a lumen extending between a distal end and a proximal end, wherein each of the plurality of tubes comprises a plurality of infusion ports extending between the inner surface and outer surface of the wall of the tubes, wherein the each of the plurality of tines of the shaft are disposed in the lumen of each of the plurality of tubes to form a plurality of limbs, and wherein the distal end of each of the plurality of limbs are attached and the proximal end of each of the plurality of limbs are attached, an inner shaft comprising a wall with an inner surface and an outer surface and a lumen extending between a distal end and a proximal end, wherein the inner elongate shaft is disposed coaxially within the lumen of the shaft and is attached to the distal end of the basket, an outer shaft comprising a wall with an inner surface and an outer surface and a lumen extending between a distal end and a proximal end, wherein the outer shaft is disposed coaxially around the inner shaft to form a fluid compartment between the inner surface of the outer shaft and the outer surface of the inner shaft, and wherein the proximal end of the limbs of the basket are connected to the fluid compartment; advancing the infusion basket at least partially through a thrombus within a vessel in a first position; deploying the basket to a second position; and simultaneously infusing a therapeutic fluid through the infusion ports of the limbs of the basket.

In some embodiments, the limbs of the basket are in a closed state in the first position and radially expand away from the longitudinal axis in the second position. In some embodiments, a fluid opening through the thrombus is created when deploying the basket to the second position.

In some embodiments, the therapeutic fluid comprises a thrombolytic agent.

In some embodiments, the method further comprises delivering light energy to the thrombus. In some embodiments, the light energy is delivered to the thrombus through a fiber optic material disposed within the lumen of the inner shaft or at least one of the plurality of tubes. In some embodiments, the light energy is delivered to the thrombus simultaneously with the infusion of the therapeutic fluid.

The details of one or more embodiments of the invention are set forth in the description below. Other features, objectives, and advantages of the invention will be apparent from the description and from the claims.

BRIEF DESCRIPTION OF THE FIGURES

The accompanying drawings, which are incorporated herein and constitute part of this specification, illustrate the presently preferred embodiments of the invention, and, together with the general description above and the detailed description given below, serve to explain the features of the invention. In the drawings:

FIGS. 5A and 5B show exemplary frames with different spiral pitches.

FIG. 6 shows an exemplary basket with fiber optic components, according to an embodiment of the present disclosure.

DETAILED DESCRIPTION OF THE INVENTION

Figure 1A:
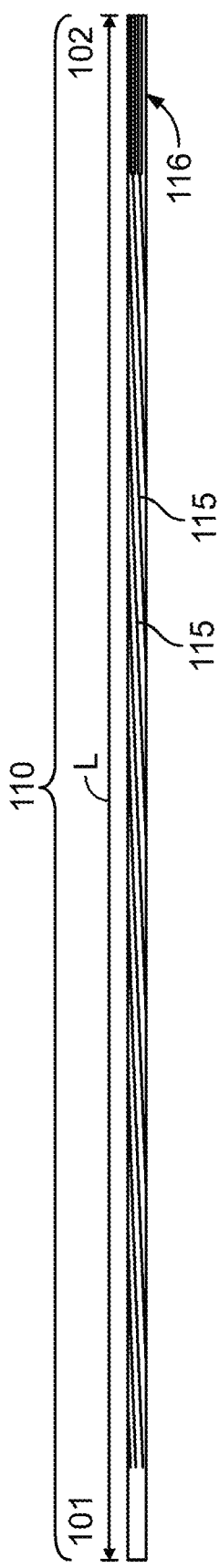
FIGS. 1A to 1C show a frame of an exemplary basket in a first (FIG. 1A) and a second position (FIG. 1B), and an assembled basket (FIG. 1C), according to an embodiment of the present disclosure.

The present invention will now be described more fully hereinafter. However, many modifications and other embodiments of the present invention set forth herein will come to mind to one skilled in the art to which the invention pertains having the benefit of the teachings presented in the foregoing descriptions. Therefore, it is to be understood that the present invention is not to be limited to the specific embodiments disclosed and that modifications and other embodiments are intended to be included within the scope of the appended claims.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the present disclosure. Thus, discussions of the features and advantages, and similar language, throughout the specification may, but do not necessarily, refer to the same embodiment.

Furthermore, the described features, advantages and characteristics of the disclosure may be combined in any suitable manner in one or more embodiments. One skilled in the relevant art will recognize, in light of the description herein, that the disclosure can be practiced without one or more of the specific features or advantages of a particular embodiment. In other instances, additional features and advantages may be recognized in certain embodiments that may not be present in all embodiments of the disclosure.

Reference throughout this specification to "one embodiment," "an embodiment," or similar language means that a particular feature, structure, or characteristic described in connection with the indicated embodiment is included in at least one embodiment of the present disclosure. Thus, the phrases "in one embodiment", "in an embodiment", and similar language throughout this specification may, but do not necessarily, all refer to the same embodiment.

In one aspect, the present disclosure relates to a mechanically deployable basket for an infusion catheter. A basket of the present disclosure is specifically designed to be deployed in complex vasculature to optimally treat vascular and arterial disease conditions such as blood clots, blood emboli, and deep vein thrombosis. The basket may comprise a shaft with a plurality of cuts along a portion of its length to form a plurality of tines that provide support for a plurality of porous tubes to form the limbs of the basket. The ends of the limbs may be attached, such that the limbs of the basket expand radially away from the longitudinal axis of the basket when the longitudinal length of the basket is reduced. The limbs may also be connected to a drug delivery system, and in this manner, baskets of the present disclosure allow for the use of both mechanical and pharmaceutical means of thrombolysis. Also provided herein are infusion catheters comprising a basket of the present disclosure. In another aspect, the present disclosure relates to methods of treatment and methods of catheter-directed thrombolysis.

As used herein, the singular form "a", "an", and "the" include plural references unless the context clearly dictates otherwise. Unless defined otherwise, all technical and scientific terms used herein have the same meanings as commonly understood by one of ordinary skill in the art.

As used herein, the terms "about" and "approximately" may be used interchangeably and is meant to encompass variations of ±20%, ±10%, ±5%, ±1%, and ±0.1% from the specified value, as such variations are appropriate.

As used herein, the term "communicate" and "communication" include, but are not limited to, the connection of fluid system elements, either directly or remotely, enabling fluid interface among and between said elements.

As used herein, the term "connectable" or "connection" refers to being able to be joined together for purposes including, but not limited to, allowing a flow of fluid. The term "connectable" can refer to being able to be joined together temporarily or permanently.

As used herein, the term "drug delivery system" refers to a device that enables the introduction of a therapeutic substance into a patient in a controlled manner. These may include, e.g., infusion pumps and other necessary components.

As used herein, the term "helical" refers to a helix or other three-dimensional curve that is disposed around the circumference of a cylinder, cone, or similar structure. The "pitch" of a helix of helical curve refers to the longitudinal distance over which the helix or helical curve completes a single revolution (360°). For example, a pitch of three inches means that the helix completes one turn every three inches, while a pitch of six inches means that the helix completes one turn every six inches. A helix or helical curve may also be described by the number of degrees of rotation that the helix or helical curve completes from its starting point to its end point. For example, a 360° helix or helical curve completes a single revolution around the circumference over its length, while a 450° helix completes one-and-a-quarter turns and a 540° helix completes one-and-a-half turns over its length.

As used herein, the terms "luer connector" and "luer adapter" refer to adapters or connectors conforming to International Standards Organization (ISO) standards 594-2.

As used herein, a "patient" or "subject" is a member of any animal species, preferably a mammalian species, optionally a human. The subject can be an apparently healthy individual, an individual suffering from a disease, or an individual being treated for a disease.

As used herein, the term "shape memory material" may comprise a shape memory alloy or shape memory polymer. These materials are characterized by pseudoelasticity, or superelasticity, which is a reversible elastic response to an applied stress that allows the material to return from a temporary deformed state to a permanent original shape after the applied stress or force is removed. Exemplary shape-memory alloys include copper-aluminum-nickel allows and nickel-titanium (nitinol) alloys.

As used herein, a "therapeutic fluid" is a fluid that that may be administered to a patient through a basket or catheter of the present disclosure. These "therapeutic fluids" may be inert and administered in conjunction with other therapeutic techniques and methods disclosed herein, or may comprise one or more therapeutic agents. A "therapeutic agent" (or "pharmaceutical", "pharmaceutically active agent", "drug" or other related term which may be used interchangeably herein) refers to an agent that that may be used for the treatment of a disease or condition (i.e., the prevention of a disease or condition, the reduction or elimination of symptoms associated with a disease or condition, or the substantial or complete elimination of a disease or condition). These agents may include thrombolytic agents that are used to dissolve blood clots including, but not limited to, fibrinolytic such as Streptokinase, Urokinase, Anistreplase, Recombinant tissue plasminogen activators, or staphylokinase, or other thrombolytic agents as known to those of ordinary skill in the art.

As used herein, the terms "treating" and "treatment" refer to the management and care of a patient having a pathology or condition by administration of one or more therapy contemplated by the present disclosure. Treating also includes administering one or more methods of the present disclosure or using any of the systems, devices or compositions of the present disclosure in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

As used herein, the term "vessel" refers to a bodily passage or tract through which a basket of the present disclosure may be disposed. This may include, e.g., the circulatory system, the digestive tract, urinary tract, biliary tract, or other passages in the body.

Figure 1B:
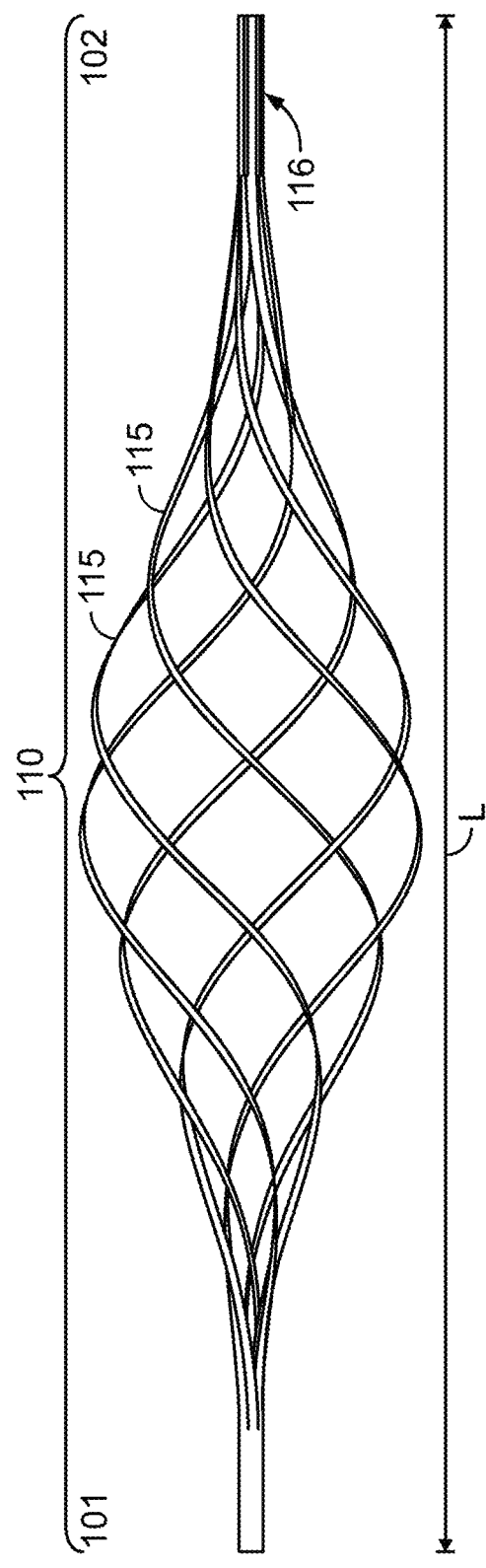
Figure 1C:
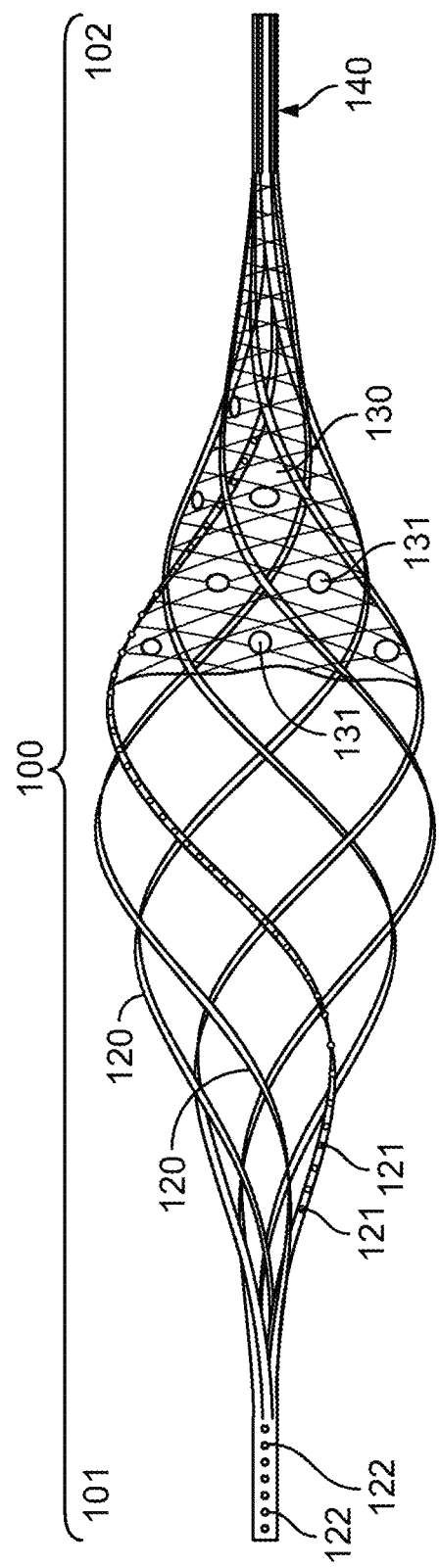
Figure 2:
FIG. 2 shows a photograph of a frame before assembly into a basket, according to an embodiment of the present disclosure.

Referring now to FIGS. 1A-C, an embodiment of a basket of the present disclosure is provided. As shown in FIG. 1A, the deployable basket comprises a frame 110. Frame 110 comprises a hollow tube or shaft with a wall with an inner surface and an outer surface and a lumen extending from its proximal end 101 to its distal end 102 and defining a longitudinal axis. The wall of the shaft has a plurality of cuts from the outer surface of the wall to the inner surface of the wall and extending longitudinally from an end, e.g., the distal end, of the shaft along a portion of its length to provide a plurality of tines 115, the ends of which are free and unattached to one another. The cuts do not extend the full length of the shaft, but rather the other end, e.g., the proximal end, is uncut in order to maintain a solid attachment point between each of the plurality of tines 115. A photograph of a frame 110 with a plurality of tines 115 is shown if FIG. 2. As can be seen, cuts extend from the left end of the shaft to form tines 115, while the right end of the shaft remains whole. The free ends of the tines 115 may be permanently or temporarily attached together to prevent movement of the free ends, particularly in a radial direction away from the longitudinal axis. For example, as shown in FIG. 1A, a cap 116 may be placed over the free ends of tines 115. With the ends of the tines joined, the frame 110 of the basket may be deployed from a closed state to an expanded state by reducing the longitudinal length L of the frame 110, i.e., by moving the proximal and distal ends closer together along the longitudinal axis, as shown in FIG. 1B. In some embodiments, the tines 115 of frame 110 expand radially away from the longitudinal axis when the longitudinal length of the frame is reduced.

A fully assembled basket 100 is shown in FIG. 1C, and it further comprises a plurality of tubes 120 disposed around each of the tines 115. The tubes may comprise a wall with an inner surface and an outer surface and a lumen extending between a distal end and a proximal end. In some embodiments, the tubes may be slipped over the free ends of tines 115 before the ends of the tines are joined. Together, the tines 115 of frame 110 and tubes 120 form the limbs of the basket 100 of the present disclosure. The free ends of the limbs may be permanently or temporarily attached to each other by joining or securing the free ends of tines 115, the tubes 120, or both. In some embodiments, the free ends of the limbs are secured by melting or gluing the ends of tubes 120 together. A cap 140 may be placed over the free ends of the limbs. It should be understood that, if the tines 115 are disposed within the lumens of tube 120, securing the free ends of tubes 120 together to prevent radial movement away from longitudinal axis of the basket 100 would likewise secure the free ends of tines 115. As discussed above, once the free ends of the tines 115 are joined, either directly or by securing the ends of tubes 120, basket 100 may be deployed to an expanded state by reducing its longitudinal length. In this way, the frame 110 provides the support for the tubes 120 and its structure dictates the manner in which the limbs of the basket 100. In some embodiments, the limbs of basket 100 expand radially away from the longitudinal axis when its longitudinal length is reduced. In this way, a basket of the present disclosure is able to mechanically open a passageway through an occluded vessel by expanding the limbs of basket 100 while the basket 100 is disposed within a thrombus.

Each of the tube 120 may be porous and comprise a plurality of ports 121 between in the inner and outer surface of the walls of the tubes 120, fluidly connecting the internal lumens of the tubes 120 to the exterior. The ends of one, multiple, or all of tubes 120 may be fluidly connected to a drug delivery system through, e.g., a catheter shaft, and the porosity of the tubes 120 allow a therapeutic to be delivered through the basket 100. The number, size, and orientation of the ports 121 may be adjusted to provide a desired infusion rate and to ensure uniform dispersion of the therapeutic fluid along the entire length of the basket 100. The ports may be evenly distributed along the length of tubes 120, or may be non-uniform. The ports may also be placed in a manner to provide directional infusion. For example, the ports may be placed on the side of the wall of tubes 120 that is further away from the central longitudinal axis of basket 100, i.e., the portion of the wall of tubes 120 that would be in contact with a clot when deployed. In this way, a basket 100 of the present disclosure is able to therapeutically dissolve a thrombus through infusion. In some embodiments, the ports 121 may be laser-drilled holes having diameters between 0.001 and 0.010 inches, with between 5 and 100 ports 121 per tube 120. In some embodiments, a tube 120 may comprise 48 ports 121 that are sized between 0.001 and 0.006 inches. The design of the ports 121 may be matched with the input flow rate requirements of a drug delivery system that is connected to one, multiple, or all of the lumens of tubes 120. By matching the flow-rates, the optimal backpressure within the tubes 120 can be created to release a therapeutic fluid in a uniform manner along their entire lengths.

Figure 3:
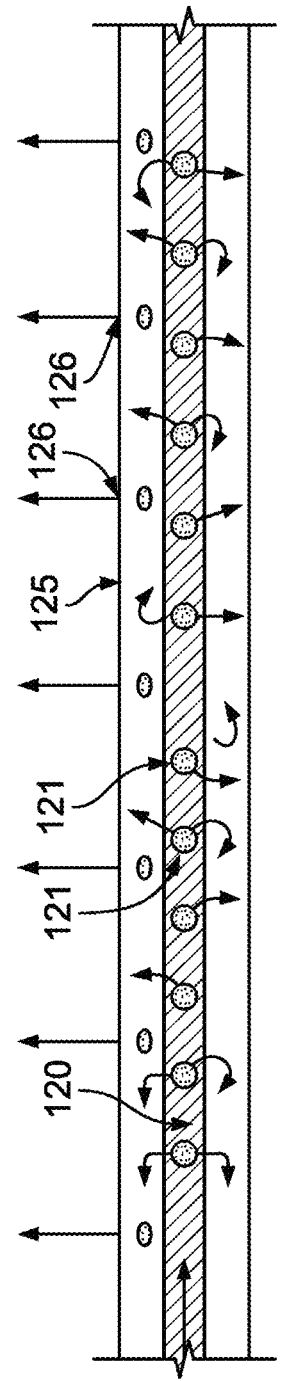
FIG. 3 shows a method for creating uniform flow along the length of an exemplary limb of a basket, according to an embodiment of the present disclosure.

In some embodiments, the basket may comprise an additional set of outer tubes 125 comprising a wall with an inner surface and an outer surface and a lumen extending between a distal end and a proximal end disposed around each of tubes 120, as shown in FIG. 3, which depicts a single limb of the basket 100. Outer tubes 125 may be sized such that a fluid compartment is formed between the inner surface of the wall of outer tubes 125 and the outer surface of the wall of tubes 120. The proximal and distal ends of outer tubes 125 may be sealed against the proximal and distal ends of tubes 120 such that the formed fluid compartment is sealed at the proximal and distal ends. Outer tubes 125 may be porous and comprise a plurality of ports 126 between in the inner and outer surface of the walls of the outer tubes, similar to the plurality of ports 121 on tubes 120. However, ports 126 may be sized and spaced such that the flow rate of a therapeutic fluid through ports 126 is less than the flow rate of the therapeutic fluid through ports 121, e.g., the cross sectional surface area of ports 126 is less than the surface area of ports 121. In this way, fluid that flows through the lumen of a tube 120 and is emitted through ports 121 accumulates within the formed fluid compartment and distributes along the longitudinal length of the limb as it is emitted through ports 126. Accordingly, even fluid distribution along the entire length of a limb is ensured. In some embodiments, the ports 126 may be laser-drilled holes having diameters between 0.001 and 0.010 inches, with between 5 and 100 ports 126 per outer tube 125.

The length of the basket 100 may be adjusted in order to provide the desired therapeutic benefits to the desired target location. In some embodiments, the basket 100 may be between two inches and eight inches in a closed state. In some embodiments, the basket 100 is approximately five inches in length in a closed state. However, as the length of the basket 100 is increased, its structural properties may be affected such that its thrombolytic performance is impaired. In such instances where a greater basket length is desired, one or more baskets 100 may be disposed adjacent to one another along the same longitudinal axis. In some embodiments, option ports 122 may be placed at the distal end 101 of the basket 100 to create a greater infusion length.

In some embodiments, the basket 100 may further comprise an optional distal catch protection basket 130 around the distal end of the basket 110. This distal catch protection basket 130 may serve as a safety net by preventing large emboli fragments from embolizing to another part of the body. This may be of particular risk when the basket 100 is placed within a large artery, such as the pulmonary artery. A membrane of a soft, thin polymer would be attached to the outside of the limbs of basket 100 to provide a webbing between each of the limbs when the basket 100 is expanded. Once expanded, the webbing forms a parachute-shaped catch that can capture particles that may float downstream. In some embodiments, the distal catch protection basket 130 may comprise holes 131 sized to allow blood flow while still allowing the distal catch protection basket 130 to capture any debris that may be generated during use of the device.

In addition to capturing these clots, the port 121 in tubes 120 at the distal end of the limbs, i.e., within the distal catch protection basket 130 may be oriented inward towards the interior space of the distal catch protection basket 130, thereby allowing maximum concentration of the infused therapeutic agent into the interior space to dissolve any captured fragments. Upon completion of the treatment, the basket can be retracted and removed from the patient, and any emboli that remains would be trapped in the distal catch protection basket 130 and could be safely removed from the body for examination. The distal catch protection basket 130 may be made of any suitable material, including, but not limited to, several varieties of polymers. For example, materials such as such as Nylon 12, polyethylene terephthalate (PET), polyether ether ketone (PEEK), polyurethanes, or a polyether block amide of various durometers. The exact durometer and thickness and hole 131 arrangement of the webbing of the distal catch protection basket 130 may be optimized for the specific size of basket 100 and desired application. The webbing could be made by any standard balloon blowing methods as known to those of ordinary skill in the art, and then cut to fit the basket and attached, or may be casted directly on the basket end.

As discussed above, the frame 115 of basket 100 is constructed from a hollow shaft with a plurality of cuts through the wall of the shaft and extending from one end along a portion of the length of the shaft. These cuts determine the resulting structural shape of the basket 100. In some embodiments, these cuts are made by a laser with a specific set of design patterns that have been optimally configured to provide open or expanded shapes to match vascular anatomy when in a deployed state. These cuts may be straight, i.e., parallel to the longitudinal axis of the tube, helical, or both straight and helical. Each of the plurality of the cuts may be congruent, i.e., identical in form, and translated around the circumference of the shaft such that they are parallel to one another along the longitudinal axis. That is, each of the tines 115 formed by the plurality of cuts may be a consistent width along their entire length. In other embodiments, each of the plurality of cuts may be incongruent, such that the tines 115 formed therefrom vary in width along their length.

Figure 4A:
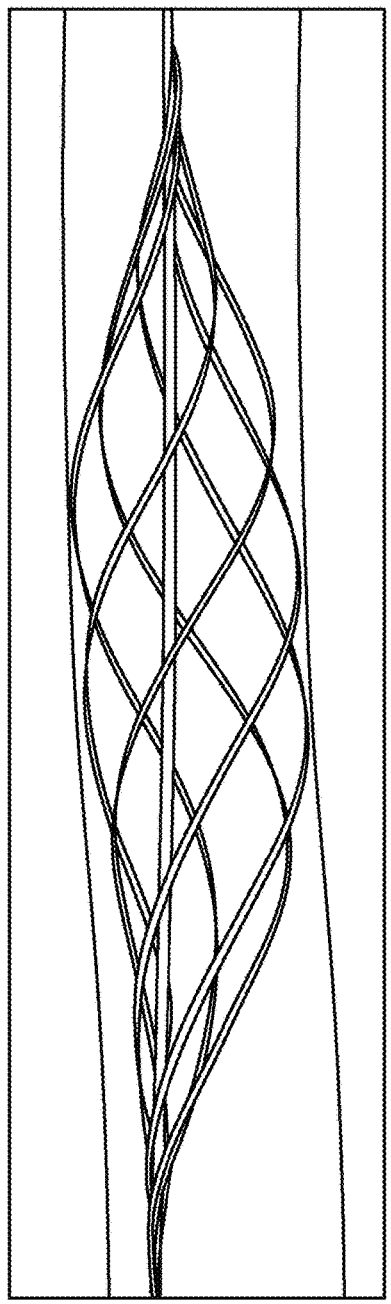
FIGS. 4A to 4C show an exemplary internal frame in an expanded state within (FIG. 4A) a straight vessel, (FIG. 4B) a curved vessel, and (FIG. 4C) a vessel mimicking the greater curvature of the pulmonary artery.
Figure 4C:
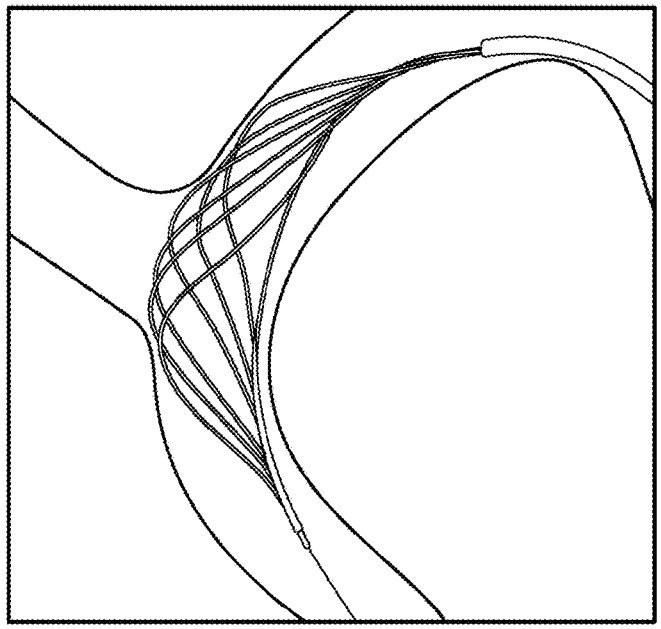
Figure 4B:
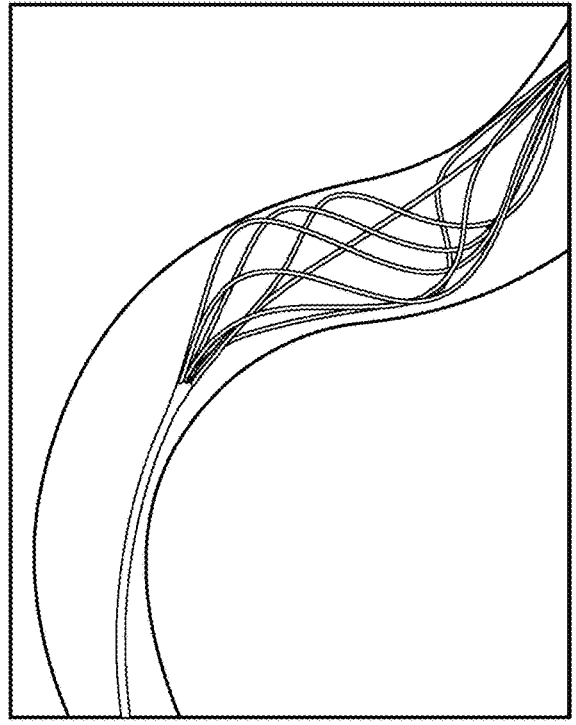

In some embodiments, the plurality of cuts are helical. In particular, it has been found that frame 110 made with a plurality of helical cuts over a portion of the length of the frame 110 creates tines 115 that provide optimal opening characteristics. As shown in FIGS. 4A to C, the resulting tines 115 from a plurality of helical cuts provides a uniform radial distribution of the arms, and creates an open passage channel within the shape of the deployed infusion basket 110 in both a straight vessel (FIG. 4A) or a curved vessel (FIG. 4B). As shown in FIG. 4C, the helical-cut frame 110 is optimally designed for deployment within the pulmonary artery, and expands to a deployed state whereby the tines 115 push outward into the greater curvature of the pulmonary artery, thus trapping a clot against the roof of the artery. This immediately restores blood flow to the affected area and provides the additional benefit of preventing accidental dislodgement of the clot.

Further, the uniform expansion of the internal frame 110, and thereby of the limbs of basket 100, along its length ensures uniform distribution of the administered therapeutic agent, and the contact between the limbs and the clot ensures direct administration of the therapeutic agent to the target area of the clot, improving clinical outcomes and speeding recoveries. The pitch of the plurality of helical cuts may be manipulated to provide the desired deployment characteristics, as shown in FIGS. 5A and B, which depicts two different frames 110 with helical cuts of differing pitch. In some embodiments, the helical cuts may have a pitch of between one inch and six inches (i.e., the cut may complete one revolution around the shaft of frame 110 per inch to one revolution per six inches.) In some embodiments, the helical cuts may have a rotation of be between 360° and 1080° over the length of the internal frame 115. In one embodiment, the plurality of helical cuts have a rotation of approximately 450° over a length of approximately 5 inches, i.e., have a pitch of approximately 4 inches. In some embodiments, the pitch of the helical cuts may vary over length of the frame 110, such that, e.g., the distal end may have a greater pitch than at other portions along the length of the frame.

In some embodiments, the frame 110 is constructed of a shape-memory material, and may be made of a nickel-titanium alloy, e.g., nitinol. However, it is to be understood that the frame 110 may be made of any suitable material as understood by those of ordinary skill in the art, and may include, e.g., stainless steel or cobalt-chrome. The frame 110 may be electropolished and/or heat set after laser cutting is done to form the tines 115. The heat setting of the frame 110 provides its permanent shape to which it returns after being deformed. In some embodiments, the frame 110 may be heat-set into a closed profile in which the tines lay flat against the longitudinal axis and essentially form the shape of the shaft. A frame 110 heat-set in this manner may be deployed to an expanded state by, as discussed above, applying a force to reduce the longitudinal length of the frame 110, and the frame 110 would return to a closed state once the force is removed. In other embodiments, the frame 110 may be heat-set at any stage of deployment, from completely closed to completely expanded. For example, if heat-set in a completely expanded state, the frame 110 could be placed into a closed state by applying a force to lengthen the longitudinal length of the frame, and the longitudinal length would shorten and the frame 110 would return to an expanded state once the force is removed. An outer sheath may be placed over a heat-set expanded deployable basket 110 to maintain a closed position while basket is maneuvered through the vasculature into position. The sheath may then be removed to allow expansion at the site of the occlusion, and then the sheath may be replaced afterwards to maintain the closed position for removal.

In some embodiments, the basket 100 may further comprise fiber optic material 150 disposed within one, multiple, or all of the lumens of tubes 120, as shown in FIG. 6. These fiber optic materials may be connected to a light-emitting device and can be used to direct light energy, e.g., laser energy, E from the limbs of basket 100 into a thrombus to provide another mechanism by which the occlusion may be broken down or removed. Thrombi within a blood vessel typically absorb light energy at a specific wavelength that may be minimally absorbed by the walls of the blood vessel. In some embodiments, the light energy emitted from the fiber optic materials may be at such a wavelength in order to enhance breakdown of a thrombus without damaging the surrounding blood vessel. By delivering light energy through the fiber optic material 150 to a thrombus, in addition to the mechanical compaction and infusion of therapeutic agents as described above, baskets and catheters of the present disclosure may reduce the time required to dissolve a thrombus, which may be over 24 hours when using conventional pharmacological methods alone. In other embodiments, the fiber optic materials may emit light energy that may be used for measurement or diagnostic purposes such as, e.g., determining the size or density of a thrombus.

Another feature of baskets of the present disclosure is the ability to provide both fluid infusion and the delivery of light energy simultaneously, which allows for baskets of the present disclosure to provide an additional cooling benefit to the treatment site. During the transmission and delivery of light as described above, excessive heat can be generated at the treatment site. Excessive heat limits the energy levels available, the duration of treatment, decreases the effectiveness of laser delivery devices, and increases the risk that damage to the tissues could occur. The design of a basket of the present disclosure allows for the infusion of fluid simultaneously with the transmission of light energy. As shown in FIGS. 6 and 7A-C, the energy and focal area of the light energy delivered by the fibers 150 is the same as where fluid is infused from the limbs of a basket of the present disclosure. The delivery of fluid simultaneously with the light energy will cool the area where the light energy is focused, allowing higher energy levels to be used, longer treatment durations, and increased overall efficiency. The cooling fluid may be a therapeutic fluid, or may be an inert, biologically acceptable fluid, such as saline. The temperature of the cooling fluid may be varied to provide different degrees of cooling effect. In some embodiments, the temperature of the cooling fluid is between 70° and 90° F.

In some embodiments, the basket 100 may be also be used to deliver radioisotopes to a tissue, and particularly a tumor or cancer. The limbs of the basket 100 may be used to carry an irradiation source and deliver said irradiation source to the tissue to be treated. The irradiation source may be, e.g., seeds, isotopes, liquid, or compositions or materials comprising such seeds, isotopes, or liquids, that emit beta and/or gamma particles. Radioisotopes such as, e.g., radioactive iodine ($I^{131}$), strontium 89, samarium 153, phosphorus 32, yttrium 90, radium 226, cesium 137, cobalt 60, iridium 192, iodine 125, and gold 198 may be used. In some embodiments, heavy shielding may be necessary to prevent radiation damage to healthy tissues as the basket or catheter is delivered through the body to the desired therapeutic site. A catheter sheath may be made of radio-opaque material such as tantalum or tungsten loaded polymers and used to surround the closed basket. When the basket has been deployed to the target site, the sheath may be retracted, exposing the basket and irradiation source, when may then be deployed to an expanded state to irradiate the site. In this way, beta and/or gamma particles may be delivered evenly to a therapeutic site, e.g., a tumor or cancer.

Figure 7A:
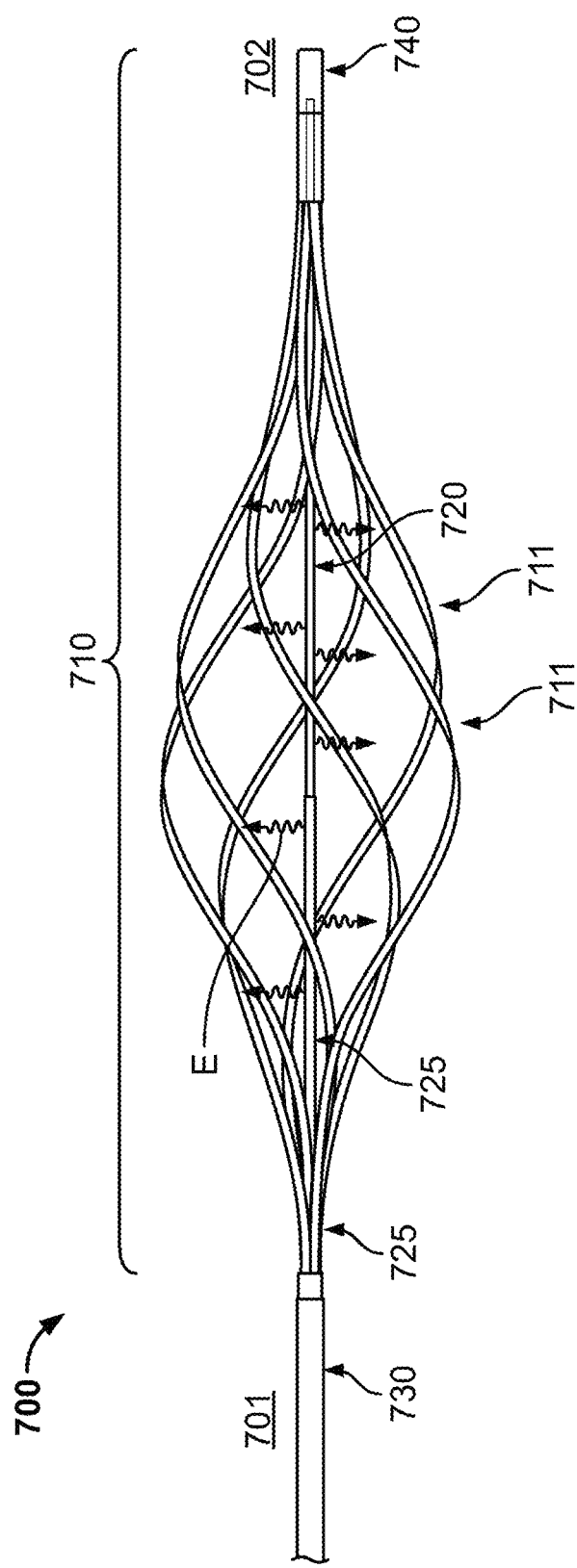
FIGS. 7A to 7C show an exemplary infusion catheter device in an open or expanded position (FIG. 7A) and closed position (FIG. 7B) in a lateral view, and in an open or expanded position in an axial view (FIG. 7C), according to an embodiment of the present disclosure.
Figure 7B:
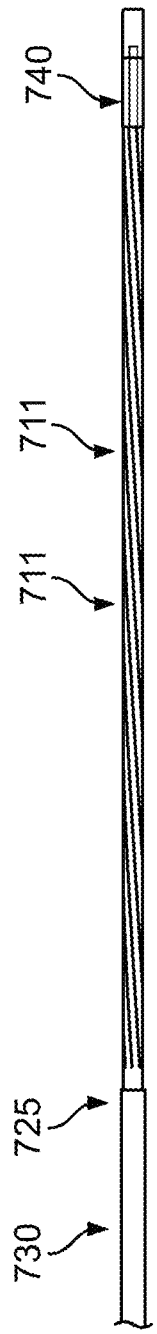
Figure 7C:
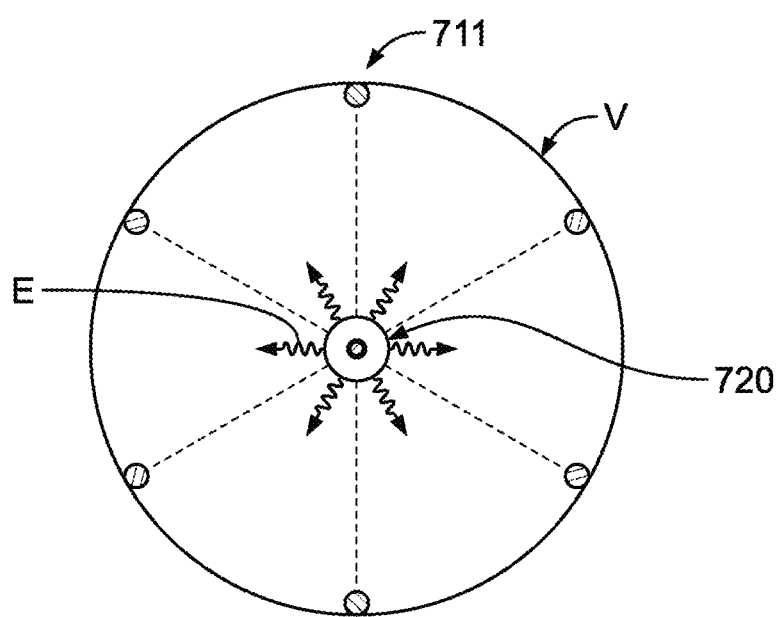

Also provided is a catheter comprising a basket of the present disclosure. Referring now to FIGS. 7A-C, a catheter 700 with a proximal end 701 and a distal end 702 comprises a basket 710 as described above comprising a plurality of limbs 711 disposed at a distal end 702 of the catheter 700. The catheter 700 further comprises an inner shaft 720 comprising a wall with an inner surface and an outer surface and a lumen extending between a distal end and a proximal end is disposed coaxially within the lumen of the frame of basket 700. This inner shaft 720 may be attached temporarily or permanently at its distal end to the distal end of the basket 710, for example by gluing or melting the inner shaft 720 to the distal end of the limbs 711 of basket 710, and/or by a distal end cap 740. The inner shaft 720 extends from the distal end of the basket 710 to beyond the proximal end of the basket 700 (not shown). The inner shaft 720 is free to move in a longitudinal direction with respect to the proximal end of the basket 700. The diameter of the lumen of inner shaft 720 may be sized to be compatible with commercial guide wires. Accordingly, a catheter 700 of the present disclosure may be threaded onto a guide wire through the internal lumen of inner shaft 720 to deploy the catheter 700 into position within a blood vessel. In some embodiments, the diameter of the lumen of inner shaft 720 is sized to be adapted for use with blood monitoring systems as known to those of skill in the art. The proximal end of the inner shaft 720 may comprise a connectable fitting, such as a luer connector, that may be connected to blood monitoring systems, including, but not limited to, a pressure transducer system as is typical in a standard hospital catheterization lab. In this way, catheters of the present disclosure allow for concurrent monitoring of a patient's vital signs during deployment and use of the device, which may allow for immediate indication of successful elimination of an occlusion. For example, the presence of an occlusion in a blood vessel may lead to increased blood pressure, and by monitoring the blood pressure during deployment and use of an catheter of the present disclosure, a successful operation may be indicated by an immediate drop in blood pressure as blood flow is restored. In some embodiments, the diameter of the internal lumen of inner shaft 720 is between 0.021 and 0.028 inches. In other embodiments, the fluid connection at the proximal end of the inner shaft 720 may be used to take blood samples.

In other embodiments, inner shaft 720 may be adapted to emit light or radiation energy in a manner similar to as described above, as noted by the arrows E extending away from inner shaft 720 in FIG. 7A. For example, a fiber optic material may be inserted through the lumen of the inner shaft 720. The fiber optic material may be connected to a light-emitting device and can be used to direct light energy from the central axis of the basket for therapeutic, measurement, or diagnostic purposes. The light energy may be emitted radially away from the central axis, or may be emitted along the longitudinal axis through the distal end of the inner shaft 720. The inner shaft 720 may also be used to carry an irradiation source and deliver said irradiation source to the tissue to be treated. In such embodiments, the limbs 711 of basket 710 may serve to center the light and/or radiation energy with the vessel, bodily passage, or tract, as shown in FIG. 7C. There the limbs 711 extend radially away from inner shaft 720 and press against the inner surface of a vessel V, thereby centering inner shaft 720 within the vessel as light or radiation energy E is emitted radially away from inner shaft 720.

An outer shaft 730 comprising a wall with an inner surface and an outer surface and a lumen extending between a distal end and a proximal end disposed coaxially around the portion of the inner shaft that extends proximally beyond the end of the basket 710 to form a fluid compartment between the inner surface of the outer shaft and the outer surface of the inner shaft. The proximal end of the limbs of the basket 710 are connected to the fluid compartment, and a fluid seal 725 may be formed between the inner shaft 720 and the proximal end of the limbs of the basket 710 such that a therapeutic fluid may flow from the fluid compartment into the lumens of the tubes of the limbs of the basket 710 and to the site of the thrombus through the plurality of ports in the tubes. The diameter of the outer shaft 730 is typically between 0.050 and 0.120 inches. The proximal end of the outer shaft 730 may terminate in a fitting, such as a luer connector, that may be connected to a drug delivery system for delivering a therapeutic fluid into the catheter.

In a first position, the limbs of the basket 710 lay flat against the inner shaft 720 in a closed manner, as shown in FIG. 7B. In this state, the outer diameter of the basket 710 is substantially the same diameter as the outer shaft 730 and distal end cap 740. The basket 710 may be expanded to a second, open position wherein the limbs expand radially outward from the longitudinal axis by moving the inner shaft 720 in a proximal direction, as shown in FIG. 7A. By moving the inner shaft 720 in a proximal direction, the longitudinal length of basket 710 is reduced and the bowing the limbs of the basket 710 bow outward away from the inner shaft 720. The basket 710 may be returned to the first position by moving the inner shaft 720 in a distal direction. Thus, a catheter 700 of the present disclosure may be delivered into a blood clot while in a closed first position, deployed into an open second position to both mechanically remove the clot and infuse therapeutic medication to the site, then returned to a closed first position for removal.

Figure 8:
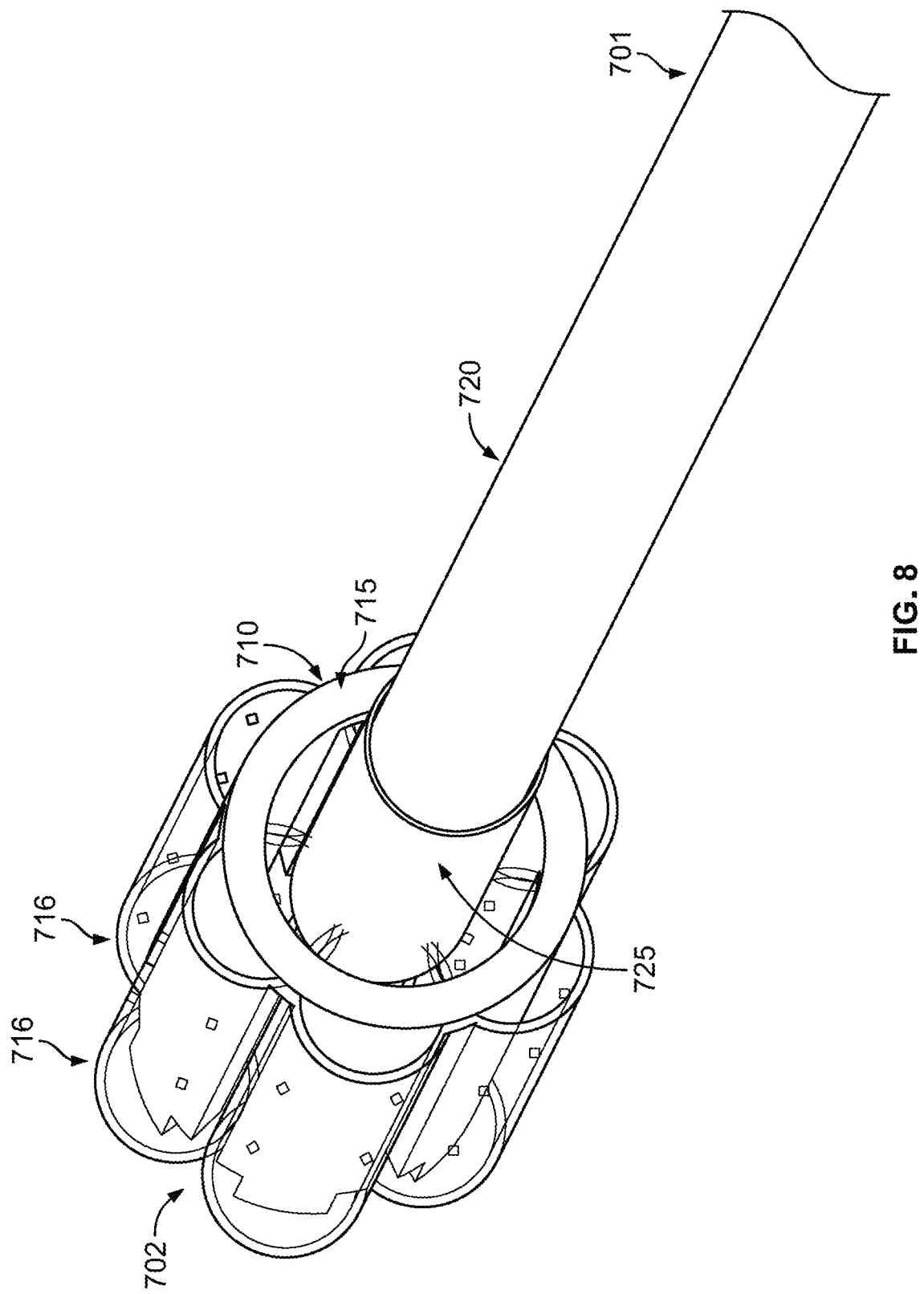
FIG. 8 shows a view of the seal assembly of an exemplary infusion catheter device, according to an embodiment of the present disclosure.

In some embodiments, catheter 700 comprises a seal 725 disposed between the inner shaft and the proximal end of the plurality of limbs as shown in the cutaway view of FIG. 8. The distal end 702 and proximal end 701 of catheter 700 and outer shaft 730 are not shown. The assembly of basket 710 comprising frame 715 and tubes 716, as discussed above, is shown. As discussed above, ends of tubes 716 may be joined together permanently or temporarily, with appropriate measures taken to ensure that the various lumens remain open during the joining process (e.g., by insertion of mandrels into the various lumens). The inner shaft 720 disposed coaxially within the internal lumen of basket 710. A seal 725 comprising a wall with an outer surface and an inner surface and a lumen from a distal end to a proximal end is disposed between the inner shaft 720 and the internal lumen of basket 710. The outer surface of the wall of seal 725 may be joined, either temporarily or permanently, to the lumen of basket 710 via, e.g., melting or gluing, thereby sealing the internal lumen of basket 710 against the outer surface of the wall of seal 725. The outer shaft 730 (not shown) would be disposed coaxially around the inner shaft 720 as described above, and the distal end of outer shaft 730 would be joined to the proximal end of the limbs of basket 710 to form a fluid seal between the fluid compartment formed between the inner surface of the wall of the outer shaft 730 and the outer wall of the inner shaft 720 and the limbs of basket 710. The inner diameter of the lumen of seal member 725 is substantially the same diameter as the outer diameter of the inner shaft 720 such that inner shaft 720 is slideable in a longitudinal direction within the lumen of seal member 725 while preventing fluid from leaking out of the distal end of the fluid compartment through the internal lumen of the basket 710. In some embodiments, the inner diameter of the lumen of seal member 725 may be slightly larger than the outer diameter of the inner shaft 720 such that a small amount of fluid may be allowed to enter the space. This small amount of fluid effectively seals the space to prevent additional fluid from leaking, while allowing inner shaft 720 to move proximally and distally along the longitudinal axis. The ability of seal member 725 to prevent fluid leakage may also be controlled by altering the length of seal member 725, such that the interface between the inner surface of its wall with the outer surface of the wall of the inner shaft 720 extends for a shorter distance, to decrease to sealing ability, or longer distance, to increase the sealing ability. Typical lengths of the sealing member 725 may be 2 to 8 inches, and can extend a portion of the length of the basket 710. As shown in FIG. 7A, the seal member 725 extends for a length of approximately half of basket 710.

In addition to a blood vessel, the baskets and catheters of the present disclosure may be utilized in any other bodily vessel or tract where a deployable basket may be disposed. This may include other areas of the body including, but not limited to, a portion of the digestive, urinary, and biliary tracts, or other vessels or passages of body.

The various tubings, shafts, and seals of the baskets and catheters of the present disclosure may be any suitable material as known to those of ordinary skill in the art, including, but not limited to, polyimide, polytetrafluoroethylene (PTFE), expanded polytetrafluoroethylene (ePTFE), polyvinylidene fluoride (PVDF), high-density polyethylene (HDPE), Nylon 6, Pebax, or nylon. The tubing may also be braided with, e.g., stainless steel, shape memory metals, or polymer fibers.

Figure 9:
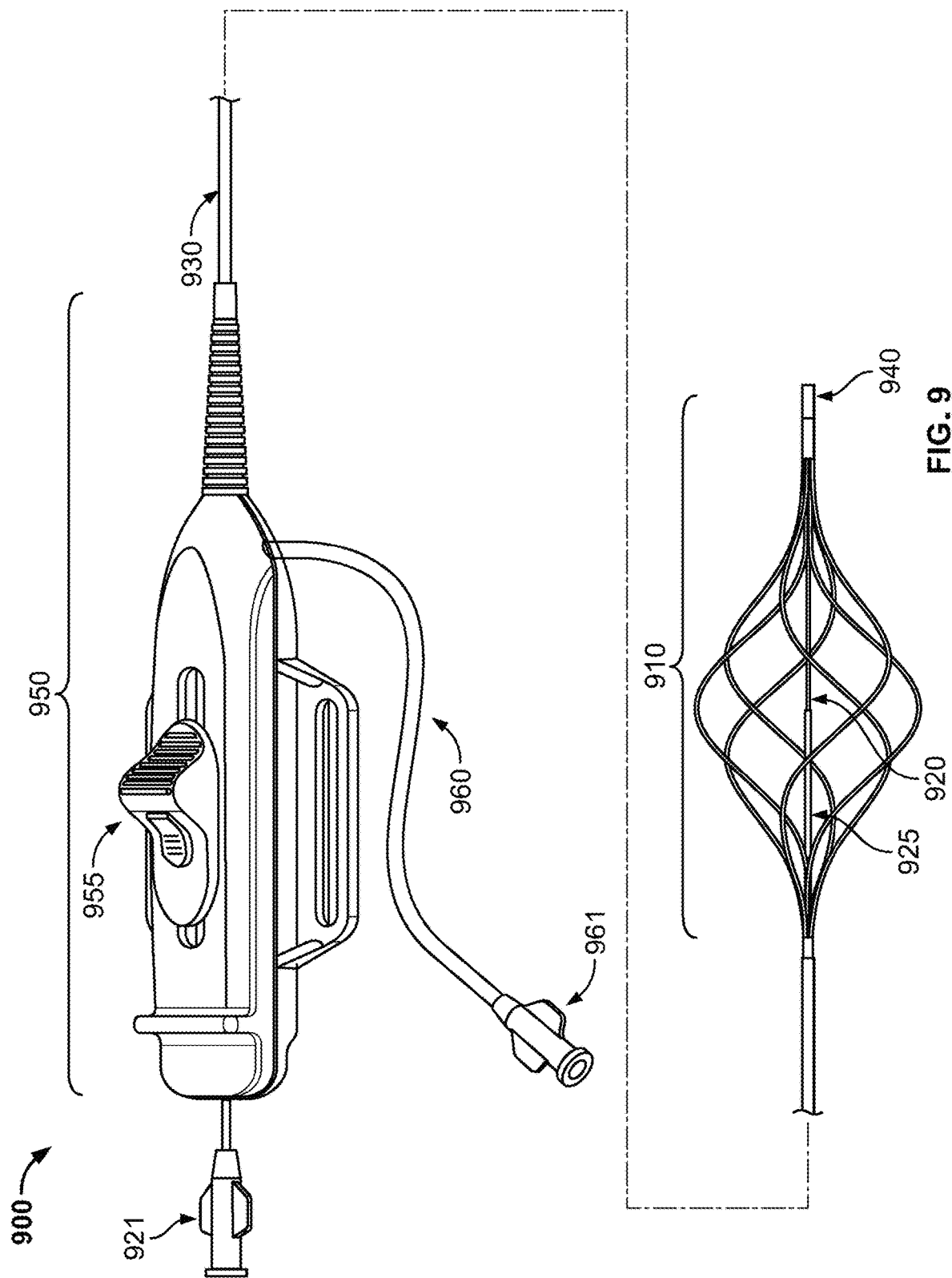
FIG. 9 shows an exemplary infusion catheter device, according to an embodiment of the present disclosure.

FIG. 9 shows an infusion catheter device according to an embodiment of the present disclosure. The distal end of infusion catheter 900 comprises a basket 910, inner shaft 920, outer shaft 930, sealing member 925, and distal end cap 940 as generally described above. The proximal end of the infusion catheter 900 comprises a handle 950. The handle further comprises a slide 955 that is connected to the proximal end of inner shaft 920 of the infusion catheter 900. The slide 955 may be used to deploy the basket to an expanded state by moving the slide in a proximal direction, thereby moving the inner shaft 920 in a proximal direction and radially expanding the basket 910 as generally described above. The proximal end of inner shaft 920 may extend beyond the end of handle 950 and terminate in a luer connector 921. This luer connected may be connected to a transducer for monitoring a patient's vital signs during use, or may be connected to other components to take blood samples. Handle 950 may also comprise an infusion shaft 960 that is fluidly connected to the proximal end of outer shaft 930. Infusion shaft 960 is terminated with a luer connector 961 that may be connected to a drug delivery system, such as an intravenous pump.

Also provided herein are methods of treatment and methods of catheter-directed thrombolysis. The method may comprise providing an infusion catheter of the present disclosure and as described above, advancing the deployable infusion basket at least partially through a thrombus within a vessel in a first position; deploying the deployable infusion basket to a second position; and simultaneously infusing a therapeutic agent through the infusion ports of the limbs of the deployable infusion basket. In some embodiments, the limbs of the deployable infusion basket are in a closed state in the first position and radially expand away from the longitudinal axis in the second position. In this manner, methods of the present disclosure provide for mechanical opening of a blood vessel while simultaneously delivering a therapeutic agent to pharmaceutically dissolve the clot. In some embodiments, light energy may be applied to the clot. Methods of the present disclosure may be employed on any vessel afflicted by a thrombus, including, but not limited to, the inferior vena cava, the superior vena cava, the iliac veins, the aorta, the pulmonary artery, or the pulmonary vein. As discussed above, the deployable infusion basket of the present disclosure is optimally designed for functioning within these large, curved vasculatures.

It will be apparent to one of ordinary skill in the art that various combinations and/or modifications and variations can be made in the infusion catheter systems and devices of the present disclosure depending upon the specific needs for operation and as dictated by the therapeutic needs of the patient. Moreover, features illustrated or described as being part of one embodiment may be used on another embodiment to yield a still further embodiment.

What is claimed is:
1. A catheter comprising:
   a basket comprising:

a shaft comprising a wall with an inner surface and an outer surface and a lumen extending between a distal end and a proximal end and defining a longitudinal axis, wherein a plurality of helical cuts along at least a portion of the shaft between the inner and outer surface of the wall form a plurality of tines,
wherein the proximal end of the shaft is uncut; and
a plurality of tubes, each tube comprising a lumen extending between a distal end and a proximal end;
wherein:
the plurality of tubes are melted together and to an outside of the shaft at the uncut proximal end of the shaft, and
each of the plurality of tines of the shaft is disposed in the lumen of each of the plurality of tubes to form a plurality of limbs;
an inner shaft disposed coaxially within the lumen of the shaft and is attached to the distal end of the basket; and
an outer shaft disposed coaxially around the inner shaft to form a fluid compartment between an inner surface of the outer shaft and an outer surface of the inner shaft,
wherein:
the proximal end of the limbs of the basket is connected to the fluid compartment, and
the connection between the proximal end of the limbs of the basket and the fluid compartment comprises a seal disposed between the inner shaft and the proximal end of the plurality of limbs, and the seal extends distally from the outer shaft.

2. The catheter of claim 1, wherein the limbs of the basket deploy from a first position to a second position when the inner shaft is moved in a proximal direction.

3. The catheter of claim 1, wherein the outer shaft comprises a luer connector connected to the proximal end of the outer shaft.

4. The catheter of claim 1, wherein the inner shaft comprises a flexible tubing connected to and extending from the proximal end of the inner shaft.

5. The catheter of claim 1, wherein the inner shaft lumen accepts a guidewire that may range in size from 0.010" in diameter to 0.45" in diameter.

6. A method of catheter-directed thrombolysis, the method comprising:
providing a catheter comprising a basket comprising:
a shaft comprising a wall with an inner surface and an outer surface and a lumen extending between a distal end and a proximal end and defining a longitudinal axis, wherein a plurality of helical cuts along at least a portion of the shaft between the inner and outer surface of the wall form a plurality of tines;
wherein the proximal end of the shaft is uncut;
a plurality of tubes, each tube comprising a lumen extending between a distal end and a proximal end, wherein each of the plurality of tubes comprises a plurality of infusion ports;
wherein:
the plurality of tubes are melted together and to an outside of the shaft at the uncut proximal end of the shaft, and
each of the plurality of tines of the shaft are disposed in the lumen of each of the plurality of tubes to form a plurality of limbs;
an inner shaft disposed coaxially within the lumen of the shaft and is attached to the distal end of the basket;
an outer shaft disposed coaxially around the inner shaft to form a fluid compartment between an inner surface of the outer shaft and an outer surface of the inner shaft,
wherein:
the proximal end of the limbs of the basket are connected to the fluid compartment, and
the connection between the proximal end of the limbs of the basket and the fluid compartment comprises a seal that extends distally from the outer shaft;
advancing the infusion basket at least partially through a thrombus within a vessel in a first position;
deploying the basket to a second position; and
simultaneously infusing a therapeutic fluid through the infusion ports of the limbs of the basket.

7. The method of claim 6, wherein the limbs of the basket are in a closed state in the first position and radially expand away from the longitudinal axis in the second position.

8. The method of claim 6, wherein a fluid opening through the thrombus is created when deploying the basket to the second position.

9. The method of claim 6, further comprising delivering light energy to the thrombus.

10. The method of claim 9, wherein the light energy is delivered to the thrombus through a fiber optic material disposed within the lumen of the inner shaft or at least one of the plurality of tubes.

11. The method of claim 9, wherein the light energy is delivered to the thrombus simultaneously with the infusion of the therapeutic fluid.

12. The method of claim 6, wherein the therapeutic fluid is distributed inside the thrombus, thereby creating pockets of therapeutic fluid within the thrombus.

13. The method of claim 6, further comprising radially expanding the limbs of the basket, thereby fragmenting the thrombus and allowing the therapeutic fluid to be delivered to and distributed in the thrombus.

14. The method of claim 13, further comprising radially expanding the limbs of the basket while infusing the therapeutic fluid through the infusion ports of the limbs of the basket.

15. The method of claim 6, comprising determining pressure from the proximal end of the shaft lumen.

* * * * *